(12) United States Patent
Tomita

(10) Patent No.: US 12,109,096 B2
(45) Date of Patent: Oct. 8, 2024

(54) ABSORBENT ARTICLE

(71) Applicant: KAO CORPORATION, Tokyo (JP)

(72) Inventor: Mina Tomita, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 809 days.

(21) Appl. No.: 17/280,585

(22) PCT Filed: Sep. 5, 2019

(86) PCT No.: PCT/JP2019/035019
§ 371 (c)(1),
(2) Date: Mar. 26, 2021

(87) PCT Pub. No.: WO2020/066531
PCT Pub. Date: Apr. 2, 2020

(65) Prior Publication Data
US 2022/0031530 A1 Feb. 3, 2022

(30) Foreign Application Priority Data

Sep. 28, 2018 (JP) .................................. 2018-185753

(51) Int. Cl.
*A61F 13/15* (2006.01)
*A61F 13/511* (2006.01)
*A61F 13/532* (2006.01)
*A61F 13/513* (2006.01)

(52) U.S. Cl.
CPC .... *A61F 13/5323* (2013.01); *A61F 13/15203* (2013.01); *A61F 13/51104* (2013.01); *A61F 13/532* (2013.01); *A61F 2013/15406* (2013.01); *A61F 13/513* (2013.01)

(58) Field of Classification Search
CPC .......... A61F 13/51104; A61F 13/15203; A61F 13/5323; A61F 13/51108; A61F 13/513; A61F 13/532; A61F 2013/15406
See application file for complete search history.

(56) References Cited

U.S. PATENT DOCUMENTS

2017/0239107 A1 8/2017 Castrogiovanni
2018/0338872 A1 11/2018 Takahashi

FOREIGN PATENT DOCUMENTS

| CN | 204863699 U | 12/2015 |
| CN | 105792785 A | 7/2016 |
| CN | 108348376 A | 7/2018 |
| EP | 2 858 826 A1 | 10/2013 |
| GB | 2559705 A | 8/2018 |

(Continued)

OTHER PUBLICATIONS

International Search Report (PCT/ISA/210) issued in PCT/JP2019/035019 mailed on Dec. 3, 2019.

*Primary Examiner* — Jacqueline F Stephens
(74) *Attorney, Agent, or Firm* — Birch, Stewart, Kolasch & Birch, LLP

(57) ABSTRACT

An absorbent article of the present invention includes an absorbent core (4) and a topsheet (2) disposed on a skin-facing surface of the absorbent core (4) and having a projecting-and-depressed structure on the skin-facing surface. The absorbent core (4) includes one or a plurality of low-basis-weight portions (41) extending in one direction and having a relatively lower basis weight than other parts of the absorbent core (4). In a plan view, the topsheet (2) includes a plurality of types of projections (24) having different sizes in an overlapping region with the low-basis-weight portions (41).

8 Claims, 7 Drawing Sheets

(56) References Cited

FOREIGN PATENT DOCUMENTS

| | | |
|---|---|---|
| GB | 2559933 A | 8/2018 |
| JP | 10-234775 A | 9/1998 |
| JP | 2009-136349 A | 6/2009 |
| JP | 2015-27348 A | 2/2015 |
| JP | 2017-60633 A | 3/2017 |
| JP | 2017-93748 A | 6/2017 |

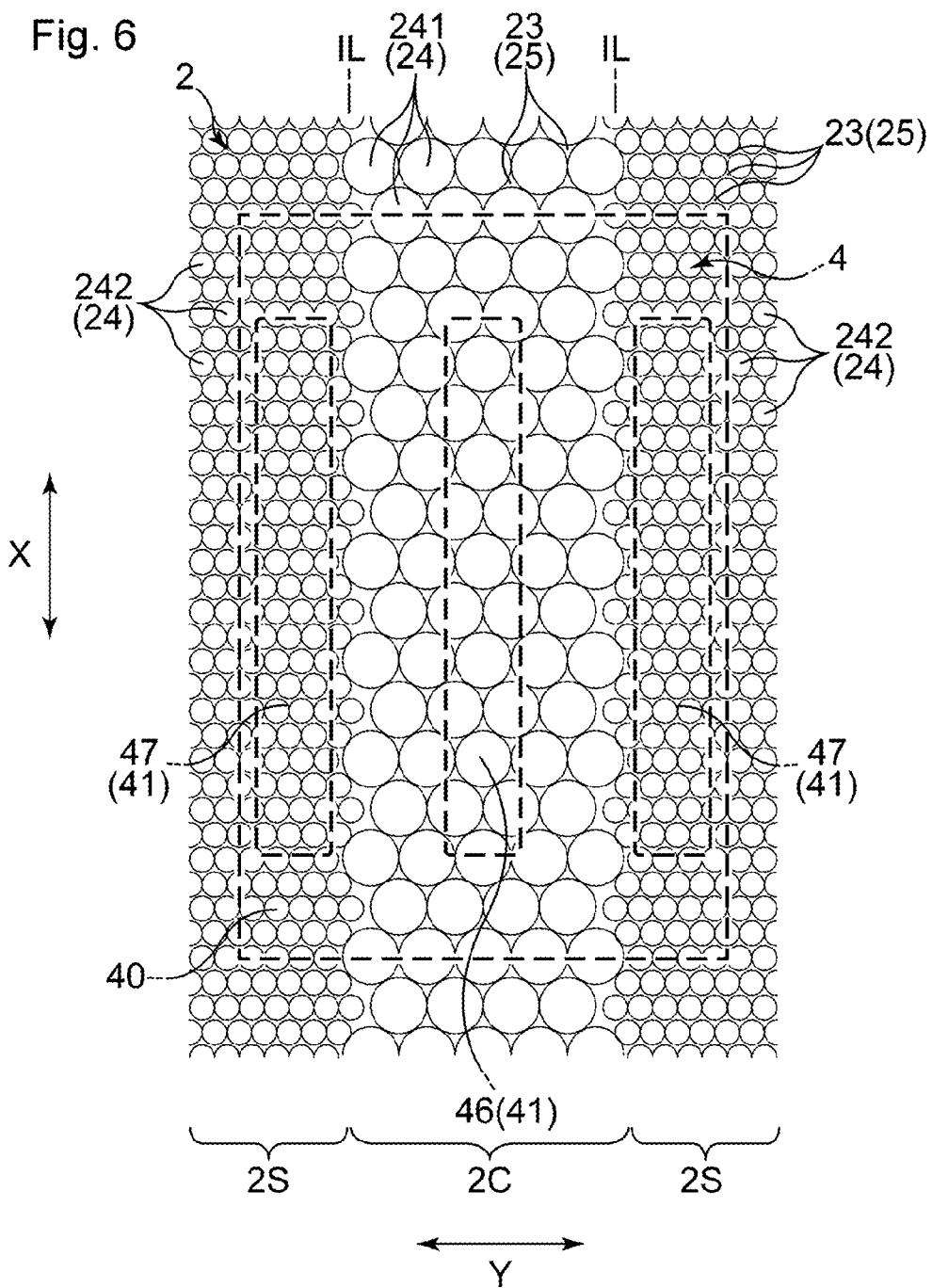

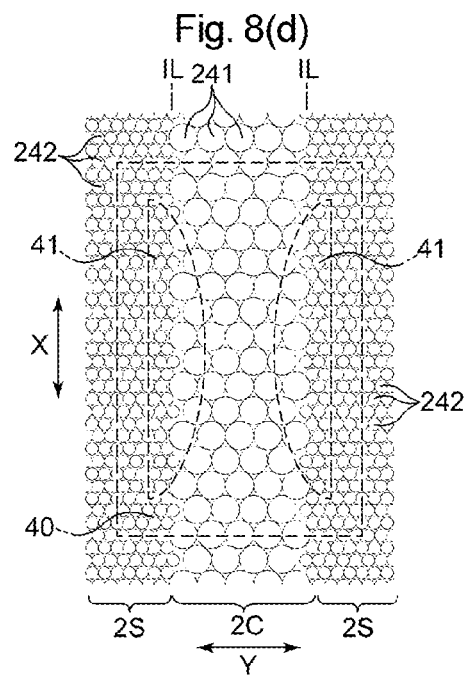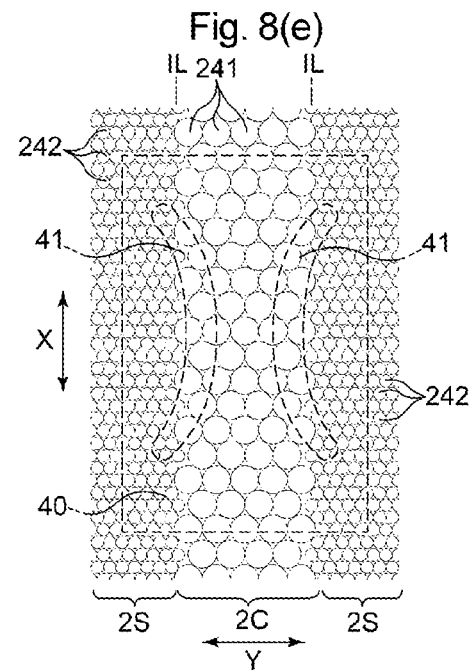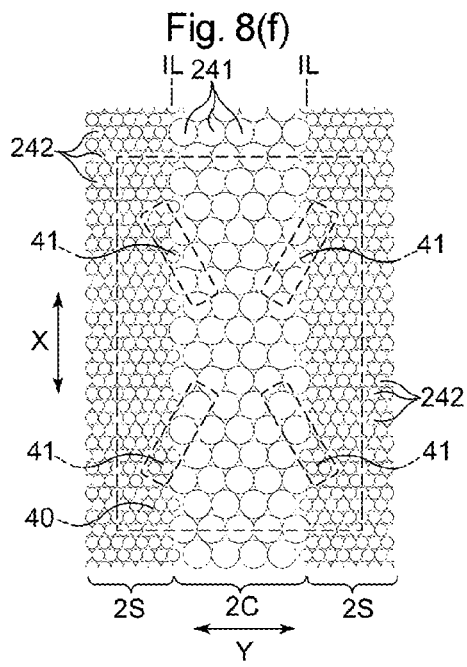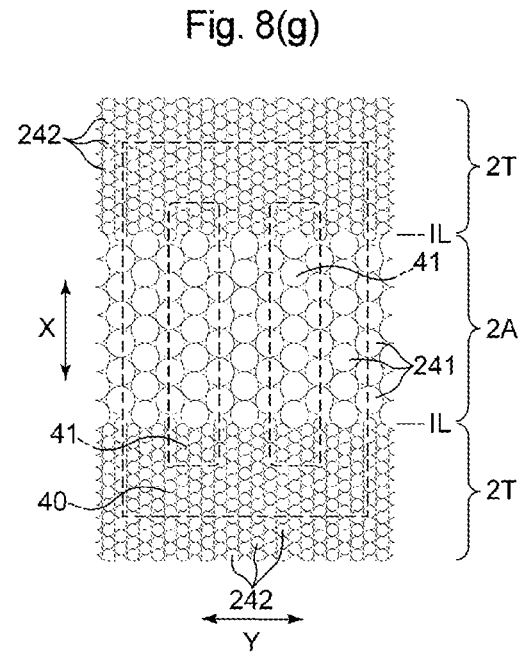

ABSORBENT ARTICLE

TECHNICAL FIELD

The present invention relates to an absorbent article.

BACKGROUND ART

Conventionally, a technique has been known in which an absorbent member is provided with a low-basis-weight portion such as a slit extending in a longitudinal direction or a width direction to diffuse excrement from an excretion position in the absorbent member. For example, Patent Literature 1 discloses an absorbent article that includes an absorbent member including a slit having a width extending in a longitudinal direction and a topsheet including a projection, the projection being disposed at a part fallen in the slit of the absorbent member in the topsheet.

As another technique, the applicant has first proposed a topsheet, as a topsheet used for an absorbent article such as a disposable diaper, in which a shape and an arrangement pattern of a joined portion are different in a central region and a pair of side regions adjacent to the central region and a shape of a projection in the central region and a shape of a projection in the side regions are different from each other (see Patent Literature 2).

CITATION LIST

Patent Literature

Patent Literature 1: Japanese Patent Laid-Open No. 2017-060633
Patent Literature 2: Japanese Patent Laid-Open No. 2017-093748

SUMMARY OF INVENTION

The present invention is to provide an absorbent article including an absorbent core and a topsheet disposed on a skin-facing surface of the absorbent core and having a projecting-and-depressed structure on the skin-facing surface. The absorbent core includes one or a plurality of low-basis-weight portions extending in one direction and having a relatively lower basis weight than other parts of the absorbent core. In a plan view, the topsheet includes a plurality of types of projections having different sizes in an overlapping region with the low-basis-weight portions.

BRIEF DESCRIPTION OF DRAWINGS

FIG. 6 is a plan view showing further another embodiment of a topsheet and an absorbent core used in the present invention.

FIGS. 8(d) to 8(g) are plan views showing further another embodiment of a topsheet and an absorbent core used in the present invention.

DESCRIPTION OF EMBODIMENTS

Figure 1:
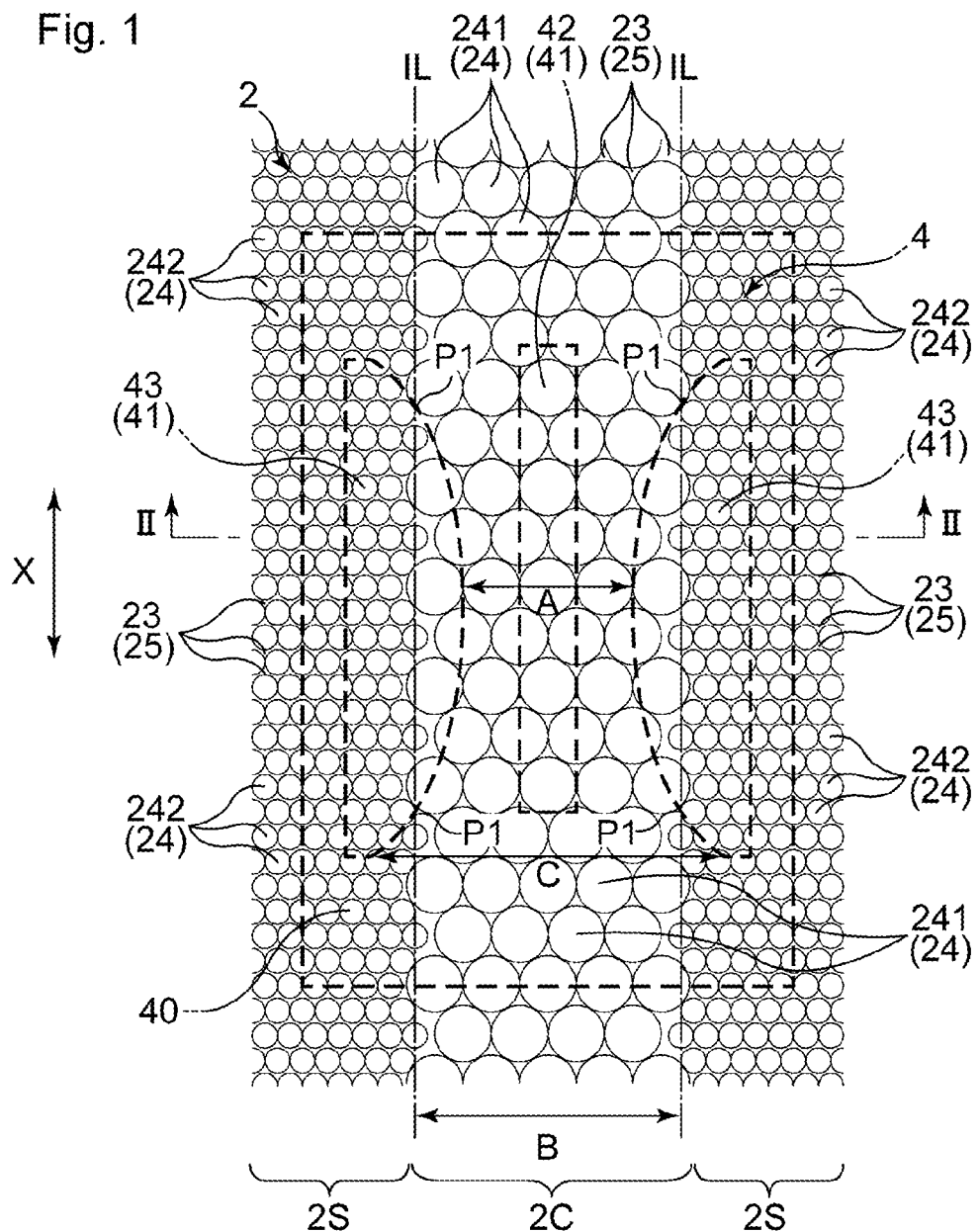
FIG. 1 is a plan view showing an embodiment of a topsheet and an absorbent core used in the present invention.

The technique disclosed in Patent Literature 1 is to cause the topsheet including the projection to fall into the slit, to restrain a collapse of a space in the slit by the projection, and to maintain a diffusion effect of a liquid by the slit, thereby preventing liquid leakage. However, even with this technique, it is not easy to reliably prevent liquid leakage. In the technique disclosed in Patent Literature 2, it has not been studied to allow the topsheet to fall into the slit of the absorbent member to prevent liquid leakage.

Accordingly, the present invention relates to an absorbent article capable of preventing leakage of excrement.

The present invention will be described below based on preferred embodiments with reference to the drawings. In general, the absorbent article of the present invention has an oblong shape having a longitudinal direction corresponding to a front-rear direction extending from an abdominal side of a wearer to a dorsal side through a crotch and a width direction orthogonal to the longitudinal direction. The absorbent article includes a crotch portion disposed in the crotch of the wearer and a front portion and a rear portion that extend in the front-rear direction. The crotch portion includes an excretion portion-facing portion disposed to face an excretion portion of the wearer when the absorbent article is worn, and the excretion portion-facing portion is usually located at a center in the longitudinal direction of the absorbent article or near the center.

The absorbent article generally includes a topsheet located on a skin-facing surface of the wearer, a backsheet located on a non-skin-facing surface, and an absorbent member interposed between the two sheets. The skin-facing surface is a surface facing the skin side of the wearer when the absorbent article is worn, that is, a side relatively close to the skin of the wearer, and the non-skin-facing surface is a surface facing the side opposite to the skin side when the absorbent article is worn, that is, a side relatively far from the skin of the wearer.

The topsheet capable of being used in the present invention includes a plurality of projections on the skin-facing surface. The details will be described below. Examples of the backsheet capable of being used in the present invention include a sparingly liquid permeable film and a spunbond/melt-blown/spunbond laminated nonwoven fabric. A plurality of micropores may be provided in the sparingly liquid permeable to impart water vapor permeability to the film. In order to further improve the feel of the absorbent article, a sheet such as a nonwoven fabric having a good texture may be laminated on an outer surface of the backsheet.

The absorbent member capable of being used in the present invention includes an absorbent core. The absorbent core is configured by, for example, a laminated fiber body of a hydrophilic fiber such as cellulose including pulp, a mixed fiber body of the hydrophilic fiber and an absorbent polymer, a stacked body of an absorbent polymer, and a layered structure in which an absorbent polymer is supported between two absorbent sheets. The absorbent core may be configured in which at least the skin-facing surface is covered with a liquid-permeable core-wrap sheet or an entire surface including the skin-facing surface and the non-skinfacing surface is covered with a core-wrap sheet. An example of the core-wrap sheet may include a thin paper made of hydrophilic fibers or a nonwoven fabric having liquid permeability. The details of the absorbent core will be described below.

In addition to the topsheet, the backsheet, and the absorbent member described above, according to a specific use of the absorbent article, leak-proof cuffs extending in a longitudinal direction may be disposed on both lateral sides in a longitudinal direction on the skin-facing surface. The leak-proof cuff generally includes a base end section and a free end. The leak-proof cuff includes the base end section on the skin-facing surface of the absorbent article, and stands up from the skin-facing surface. The leak-proof cuff is made of a liquid-resistant or water-repellent and breathable material. An elastic member made of such as a rubber thread may be disposed in a stretched state at or near the free end of the leak-proof cuff. When the elastic member is contracted in a state where the absorbent article is worn, the leak-proof cuff stands up toward the wearer's body, and the liquid excreted on the topsheet travels on the topsheet, thereby effectively preventing the liquid from leaking out of the absorbent article in the width direction.

The absorbent article may further include an adhesive layer on the non-skin-facing surface. The adhesive layer is used to fix the absorbent article to underwear or another absorbent article in a state where the absorbent article is worn.

Examples of the absorbent article having the configuration described above include open-style disposable diapers, pull-on disposable diapers, sanitary napkins, and incontinence pads, but are not limited thereto.

Figure 2:
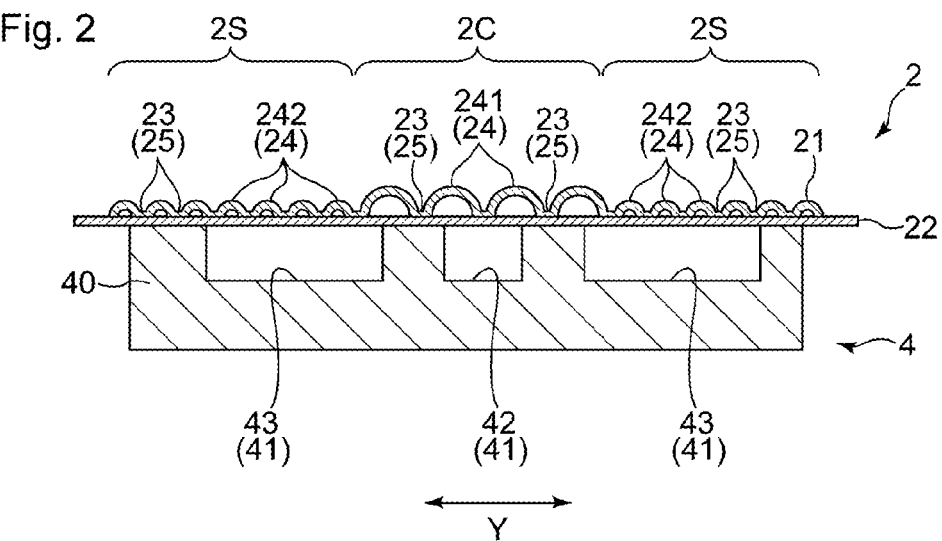
FIG. 2 is a cross-sectional view taken along line II-II in FIG. 1.

FIGS. 1 and 2 show an example of a topsheet and an absorbent core used in an absorbent article of the present invention. FIGS. 1 and 2 show a state in which a topsheet 2 having a projecting-and-depressed structure is disposed on a skin-facing surface of an absorbent core 4. The absorbent core 4 has a rectangular shape that is long in a longitudinal direction X or a shape in which both lateral sides in the longitudinal direction X is narrowed inward in a width direction Y. Preferably, the absorbent core 4 has an hourglass shape in which a central portion in the longitudinal direction X located in a crotch region is narrowed inward and an oblong shape that is long in the longitudinal direction X. The absorbent core 4 includes a plurality of low-basis-weight portions 41 extending in one direction and having a relatively low basis weight as compared with other portions of the absorbent core 4. A basis weight of the low-basis-weight portions 41 may be zero. A high-basis-weight portion 40 having a relatively higher basis weight than the low-basis-weight portions 41 is provided around the low-basis-weight portions 41. A skin-facing surface of each low-basis-weight portion 41 is located at a position lower than a skin-facing surface of the high-basis-weight portion 40. In other words, on the skin-facing surface of the absorbent core 4, a step is formed between the high-basis-weight portion 40 and the low-basis-weight portion 41. Therefore, the skin-facing surface of the absorbent core 4 has a projecting-and-depressed structure.

The low-basis-weight portion 41 is preferably disposed on an excretion portion-facing portion that is disposed to face an excretion portion of a wearer. Further, the low-basis-weight portion 41 is located at a center in the width direction Y of the absorbent core 4 and preferably includes a central low-basis-weight portion 42 extending in the longitudinal direction X and a pair of side low-basis-weight portions 43 and 43 that are located on laterally outer sides in the width direction Y from the central low-basis-weight portion 42 and extend in the longitudinal direction X.

As shown in FIG. 1, the central low-basis-weight portion 42 has both lateral side edges parallel to each other and extends in the longitudinal direction X with a constant width. On the other hand, regarding each of the side low-basis-weight portions 43, one lateral side edge, which is located on an outer side in the width direction Y, of two lateral side edges extends linearly in the longitudinal direction X, and the other lateral side edge located on an inner side in the width direction Y is curved in an arc shape that is projected inward in the width direction. Therefore, a distance between the two side low-basis-weight portions 43 and 43 is longer at an end portion in the longitudinal direction X than at a central portion in the longitudinal direction X.

The topsheet 2 has a layered structure as shown in FIG. 2 in which an upper nonwoven fabric 21 located on a skin side of the wearer and a lower nonwoven fabric 22 located on a side far from the skin of the wearer are joined to each other at a plurality of joined portions 23. The upper nonwoven fabric 21 forms a large number of projections 24 that protrude in a direction away from the lower nonwoven fabric 22 at parts other than the joined portions 23. As a result, the upper nonwoven fabric 21 forming the skin-facing surface of the topsheet 2 is formed with a projecting-and-depressed structure having undulations. On the other hand, a non-skin-facing surface of the topsheet 2 is substantially flat.

As shown in FIG. 2, portions of the projection 24 located between the plurality of joined portions 23 in the upper nonwoven fabric 21 are formed in an upward projected shape. A space is formed inside the projection 24 that is not filled with a forming material of the topsheet 2. In other words, the projection 24 is hollow. The joined portion 23 located between the projections 24 adjacent to each other forms a bottom of a depression 25 of the topsheet 2 having the projecting-and-depressed structure. The joined portion 23 is generally formed by embossing with or without heat, or by ultrasonically embossing, the upper nonwoven fabric 21 and the lower nonwoven fabric 22 in a laminated state.

As shown in FIGS. 1 and 2, the topsheet 2 is formed by a central region 2C and a pair of side regions 2S and 2S located on both sides of the central region 2C. The central region 2C is located at the central portion in the width direction Y, and extends in the longitudinal direction X. The pair of side regions 2S and 2S is adjacent to the central region 2C, and extend in the longitudinal direction X. When a leak-proof cuff is disposed on the absorbent article, the side region 2S preferably substantially coincides with an overlap position with a side sheet forming the leak-proof cuff.

A plurality of types of projections 24 having different sizes are formed on the topsheet 2. "The sizes of the projections are different from each other" means that heights of the projections are different from each other, areas of the projections are different from each other in a plan view, or both the heights and the areas of the projections are different from each other. As shown in FIG. 1, the topsheet 2 includes a plurality of first projections 241 disposed in the central region 2C and a plurality of second projections 242 disposed in the side region 2S. The first projections 241 and the second projections 242 are different in height and area in a plan view from each other. Specifically, the height of the first projections 241 is higher than the height of the second projections 242. In addition, the area in a plan view of the first projections 241 is larger than the area in a plan view of the second projections 242. The first projections 241 are disposed over the entire skin-facing surface of the central region 2C in a scattered pattern and a regular pattern. On the other hand, the second projections 242 are disposed over the entire skin-facing surface of the side regions 2S in a scattered pattern and a regular pattern.

As shown in FIG. 1, a boundary IL between the central region 2C and the side region 2S in the topsheet 2 intersects with the curved lateral side edge located on an inner side in the width direction Y of each of the side low-basis-weight portions 43 formed in the absorbent core 4 at two intersections P1 and P1. Therefore, the topsheet 2 includes two types of projections, for example, the first projections 241 and the second projections 242 in an overlapping region with the side low-basis-weight portion 43 when viewed in a plan view. In the overlapping region with the side low-basis-weight portion 43, all or a part of each of the first projections 241 exists, and similarly, all or a part of each of the second projections 242 exists.

When viewed in a plan view, the topsheet 2 includes only the first projections 241 in an overlapping region with the central low-basis-weight portion 42. In the overlapping region with the central low-basis-weight portion 42, all or a part of each of the first projections 241 exists.

Figure 3:
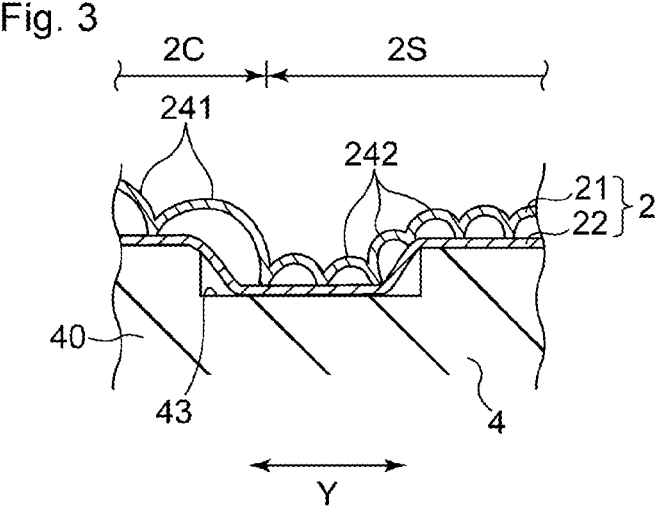
FIG. 3 is an enlarged cross-sectional view of a state in which a low-basis-weight portion of one side region in FIG. 1 absorbs a body fluid.

Since the low-basis-weight portions 42 and 43 of the absorbent core 4 and the projections 241 and 242 of the topsheet 2 are disposed in the above-described relation, according to the absorbent article of the present embodiment, advantageous effects are obtained that excrement is easily induced to the low-basis-weight portions formed in the absorbent core 4 and the excrement induced into the low-basis-weight portions is prevented from leaking to the outside of the low-basis-weight portions. Such effects will be described with reference to FIG. 3. FIG. 3 shows a state in which the absorbent core 4 absorbs excrement and swells at the position of the side low-basis-weight portion 43. In such a state, due to the swelling of the absorbent core 4, the topsheet 2 located on the side low-basis-weight portion 43 is deformed along the skin-facing surface of the absorbent core 4. As a result, the projections of the topsheet 2 are located in a depressed space defined by the side low-basis-weight portion 43. As described above, since the first projections 241 and the second projections 242 exist in the overlapping region of the topsheet 2 with the side low-basis-weight portion 43, the first projections 241 and the second projections 242 exist in the depressed space, which is defined by the side low-basis-weight portion 43, in the state shown in FIG. 3. As described above, since the first projection 241 and the second projection 242 are different in size from each other, the first projection 241 and the second projection 242 existing in the depressed space defined by the side low-basis-weight portion 43 are different in existence form from each other.

Specifically, as shown in FIG. 3, the first projection 241 having a relatively large size exists in the depressed space with a relatively gentle slope. In contrast, the second projection 242 having a relatively small size exists in the depressed space with a relatively steep slope. As described above, due to the difference in the degree of slope between the first projection 241 and the second projection 242, the excrement can be smoothly induced into the depressed space defined by the side low-basis-weight portion 43 and the leakage of the excrement from the space is effectively prevented. The reason is as follows.

As described above, the first projection 241 exists in the depressed space with a relatively gentle slope. The excrement is smoothly induced into the depressed space along such a gentle slope. However, from the opposite viewpoint, the gentle slope allows excrement located in the space to leak out of the space. However, according to the present embodiment, since the second projection 242 also exists in the depressed space with a relatively steep slope, the excrement located in the space is effectively prevented from leaking out of the space by the second projection 242.

From the viewpoint of making the above effect more remarkable, when the side low-basis-weight portion 43 is viewed in the width direction Y, the second projection 242 having a relatively small size is preferably located on the outer side in the width direction Y, and the first projection 241 having a relatively large size is preferably located on the central side in the width direction Y. Particularly, in the present embodiment, the height and the area in a plan view of the first projection 241 are larger than the height and the area in a plan view of the second projection 242. In the embodiment shown in FIG. 3, a length in the width direction of the second projection 242 is shorter than a length in the width direction of the first projection 241. With such a configuration, the excrement excreted near the central portion in the width direction of the absorbent core 4 is smoothly induced into the depressed space defined by the side low-basis-weight portion 43, and the excrement induced into the space hardly leaks from the outside of the absorbent core 4 in the width direction.

From the viewpoint of further facilitating the effect of preventing the leakage to the outside in the width direction Y, when attention is paid to the side low-basis-weight portion 43 which is one low-basis-weight portion 41, regarding the first projection 241 and the second projection 242 located in the overlapping region with the side low-basis-weight portion 43, the length in the width direction Y of the first projection 241 is preferably 2 mm or more and more preferably 4 mm or more, and is preferably 15 mm or less and more preferably 10 mm or less. On the other hand, the length in the width direction Y of the second projection 242 is preferably 1 mm or more and more preferably 2 mm or more, and is preferably 10 mm or less and more preferably 5 mm or less. The widest length in the width direction Y of the low-basis-weight portion 41 is preferably 7 mm or more and more preferably 10 mm or more, and is preferably 40 mm or less and more preferably 20 mm or less.

From the same viewpoint, as shown in FIG. 1, when the distance between the pair of side low-basis-weight portions 43 and 43 at the central portion in the longitudinal direction X is defined as A, the distance between the pair of side low-basis-weight portions 43 and 43 at the end portion in the longitudinal direction X is defined as C, and the width of the central region 2C is defined as B, a relation of A<B<C is preferably established.

The distance A is preferably 10 mm or more and more preferably 15 mm or more, and is preferably 50 mm or less and more preferably 30 mm or less.

The distance C is preferably 40 mm or more and more preferably 50 mm or more, and is preferably 80 mm or less and more preferably 60 mm or less.

The width B is preferably 20 mm or more and more preferably 30 mm or more, and is preferably 80 mm or less and more preferably 60 mm or less.

In addition, from the viewpoint of improving diffusion of excrement in a region other than the overlapping region with the central low-basis-weight portion 42 in the central region 2C, a total area of the joined portions 23 surrounding one first projection 241 disposed in the central region 2C is preferably larger than a total area of the joined portions 23 surrounding one second projection 242 disposed in the side regions 2S. The area of the joined portions 23 is an area of a region surrounded by the contour of the joined portions 23. The number of joined portions 23 surrounding the first projection 241 is preferably 4 or more and more preferably 6 or more, and is preferably 20 or less and more preferably 16 or less. The joined portion 23 surrounding the first projection 241 is preferable to have a long shape in the longitudinal direction of the side low-basis-weight portion 43 from the viewpoint of diffusing excrement along the side low-basis-weight portion 43.

The number of joined portions 23 surrounding the second projection 242 is preferably 3 or more and more preferably 5 or more, and is preferably 12 or less and more preferably 10 or less.

The total area of the joined portions 23 surrounding the first projection 241 is preferably 4 mm$^2$ or more and more preferably 6 mm$^2$ or more, and is preferably 50 mm$^2$ or less and more preferably 30 mm$^2$ or less.

The total area of the joined portions 23 surrounding the second projection 242 is preferably 3 mm$^2$ or more and more preferably 5 mm$^2$ or more, and is preferably 20 mm$^2$ or less and more preferably 15 mm$^2$ or less.

Other embodiments of the present invention will be described below with reference to FIG. 4 and FIGS. 6 to 8. In the embodiment shown in FIG. 4 and FIGS. 6 to 8, components different from those of the above-described embodiment will be mainly described, and the same components will be denoted by the same reference numerals and will not be described. The description of the above-described embodiment is appropriately applied to the components which are not particularly described.

Figure 4:
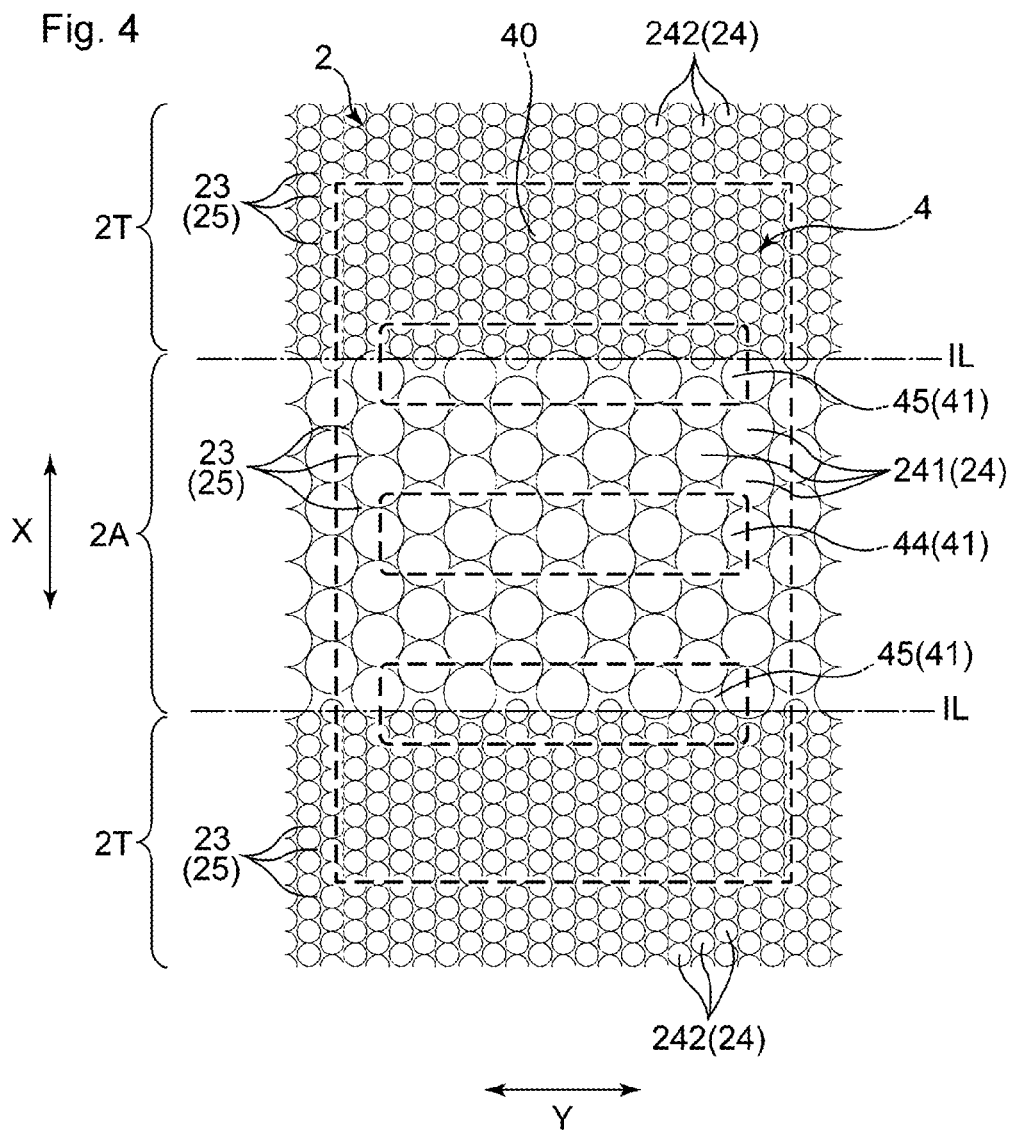
FIG. 4 is a plan view showing another embodiment of a topsheet and an absorbent core used in the present invention.

FIG. 4 shows another embodiment of a topsheet and an absorbent core used in the absorbent article of the present invention. An absorbent core 4 includes a plurality of low-basis-weight portions 41 extending in the width direction Y. In the embodiment shown in FIG. 4, the low-basis-weight portions 41 include a central low-basis-weight portion 44 located at a center in the longitudinal direction X of the absorbent core 4 and extending in the width direction Y and a pair of end low-basis-weight portions 45 and 45 located on front-rear outer sides in the longitudinal direction X from the central low-basis-weight portion 44 and extending in the width direction Y. The central low-basis-weight portion 44 is a first low-basis-weight portion 41, and each of the end low-basis-weight portions 45 is a second low-basis-weight portion 41. The central low-basis-weight portion 44 and each of the end low-basis-weight portions 45 have a constant width and extend in the width direction Y.

A topsheet 2 shown in FIG. 4 includes a central region 2A and a pair of end regions 2T and 2T located on both sides of the central region 2A. The central region 2A is located at a central portion in the longitudinal direction X, and extends in the width direction Y. The central region 2A is preferably disposed on an excretion portion-facing portion facing an excretion portion of the wearer. The pair of end regions 2T and 2T are adjacent to both ends in the longitudinal direction X of the central region 2A, and extend in the width direction Y.

In the topsheet 2 shown in FIG. 4, a projection 24 includes a plurality of first projections 241 disposed in the central region 2A and a plurality of second projections 242 disposed in the end regions 2T. The first projections 241 are relatively large projections, and are disposed in the central region 2A. The second projections 242 are relatively small projections, and are disposed in both end regions 2T and 2T.

In the topsheet 2 shown in FIG. 4, a boundary IL between the central region 2A and the end region 2T is located on each of the end low-basis-weight portions 45. Therefore, the topsheet 2 includes two types of projections, for example, the first projections 241 and the second projections 242 in an overlapping region with each of the end low-basis-weight portions 45 when viewed in a plan view.

When viewed in a plan view, the topsheet 2 includes only the first projections 241 in an overlapping region with the central low-basis-weight portion 44. In the overlapping region with the central low-basis-weight portion 44, all or a part of each of the first projections 241 exists.

Figure 5:
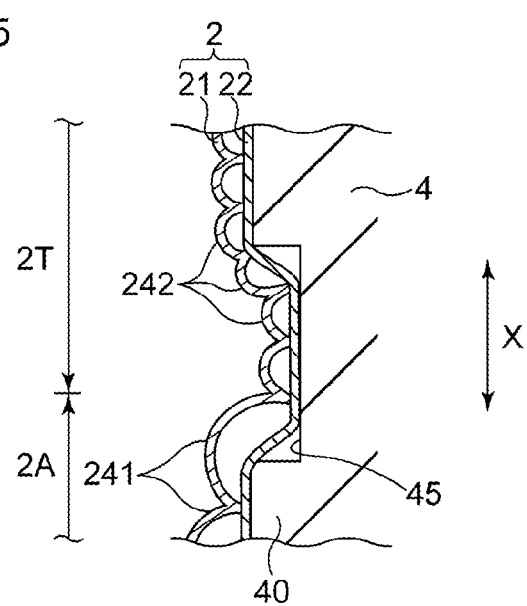
FIG. 5 is an enlarged cross-sectional view of a state in which a low-basis-weight portion of one end region in FIG. 4 absorbs a body fluid.

FIG. 5 shows a state in which the absorbent core 4 absorbs excrement and swells at the position of the end low-basis-weight portion 45. In such a state, due to the swelling of the absorbent core 4, the topsheet 2 located on the end low-basis-weight portion 45 is deformed along the skin-facing surface of the absorbent core 4. Since the first projections 241 and the second projections 242 exist in the overlapping region with the end low-basis-weight portion 45, the first projections 241 and the second projections 242 exist in a depressed space, which is defined by the end low-basis-weight portion 45, in the state shown in FIG. 5. The first projection 241 having a relatively large size exists in the depressed space with a relatively gentle slope. In contrast, the second projection 242 having a relatively small size exists in the depressed space with a relatively steep slope. Under such a state, the excrement can be smoothly induced into the depressed space along the gentle slope by the first projection 241. Since the second projection 242 also exists in the depressed space with a relatively steep slope, the excrement induced into the space is effectively prevented from leaking out of the space by the second projection 242. From the viewpoint of making the above effect more remarkable, when the end low-basis-weight portion 45 is viewed in the longitudinal direction X, the second projection 242 having a relatively small size is preferably located on the outer side in the longitudinal direction X, and the first projection 241 having a relatively large size is preferably located on the central side in the longitudinal direction X. As described above, due to the difference in the degree of slope between the first projection 241 and the second projection 242, the excrement can be smoothly induced into the depressed space defined by the end low-basis-weight portion 45 and the leakage of the excrement from the space is effectively prevented.

From the viewpoint of further facilitating the effect of preventing the leakage to the outside in the longitudinal direction X, when attention is paid to one end low-basis-weight portion 45 which is located at the end portion in the longitudinal direction X in the plan view shown in FIG. 4, regarding the first projection 241 and the second projection 242 located in the overlapping region with the end low-basis-weight portion 45, the length in the longitudinal direction X of the second projection 242 located on the outer side in the longitudinal direction X is preferably shorter than the length in the longitudinal direction X of the first projection 241 located on the central side in the longitudinal direction X. The length in the longitudinal direction X of the first projection 241 is preferably 2 mm or more and more preferably 4 mm or more, and is preferably 15 mm or less and more preferably 10 mm or less. On the other hand, the length in the longitudinal direction X of the second projection 242 is preferably 1 mm or more and more preferably 2 mm or more, and is preferably 10 mm or less and more preferably 5 mm or less. In each of the central low-basis-weight portion 44 and the end low-basis-weight portion 45, the length in the longitudinal direction X is preferably 5 mm or more and more preferably 7 mm or more, and is preferably 30 mm or less and more preferably 15 mm or less.

In an embodiment shown in FIG. 6, an absorbent core 4 includes a plurality of low-basis-weight portions 41 extending in the longitudinal direction X and not intersecting with each other. The plurality of low-basis-weight portions 41 includes a central low-basis-weight portion 46 located at a center in the width direction Y of the absorbent core 4 and extending in the longitudinal direction X and a pair of side low-basis-weight portions 47 and 47 located on laterally outer sides in the width direction Y from the central low-basis-weight portion 46 and extending in the longitudinal direction X. The central low-basis-weight portion 46 is a first low-basis-weight portion 41, and each of the side low-basis-weight portions 47 is a second low-basis-weight portion 41. The central low-basis-weight portion 46 and each of the side low-basis-weight portions 47 have a constant width and extend in the longitudinal direction X.

A topsheet 2 shown in FIG. 6 includes a central region 2C and a pair of side regions 2S and 2S located on both sides of the central region 2C. The central region 2C is located at a central portion in the width direction Y, and extends in the longitudinal direction X. The pair of side regions 2S and 2S are adjacent to the central region 2C, and extend in the longitudinal direction X.

In the topsheet 2 shown in FIG. 6, a projection 24 includes a plurality of first projections 241 disposed in the central region 2C and a plurality of second projections 242 disposed in the side regions 2S. The first projections 241 having a relatively large size are disposed in the central region 2C, and the second projections 242 having a relatively small size are disposed in both lateral side regions 2S and 2S. A length in the width direction of the first projection 241 differs from a length in the width direction of the second projection 242, and the second projection 242 is shorter than the first projection 241.

In the topsheet 2 shown in FIG. 6, a boundary IL between the central region 2C and the side region 2S is located between the central low-basis-weight portion 46 and each of the side low-basis-weight portions 47. Therefore, the topsheet 2 includes only the first projections 241 having a relatively large size in an overlapping region with the central low-basis-weight portion 46 when viewed in a plan view. In such a region, all or a part of each of the first projections 241 exists. On the other hand, the topsheet 2 includes only the second projections 242 having a relatively small size in an overlapping region with each of the side low-basis-weight portions 47. In such a region, all or a part of each of the second projections 242 exists. As described above, in the embodiment shown in FIG. 6, when attention is paid to the central low-basis-weight portion 46 and the side low-basis-weight portion 47 adjacent to each other in the width direction Y, the first projections 241 disposed in the overlapping region with the central low-basis-weight portion 46 is different in size of the projection from the second projections 242 disposed in the overlapping region with the side low-basis-weight portion 47. In other words, the topsheet 2 includes two types of projections 24 having different sizes in an overlapping region with the low-basis-weight portion 41. According to the absorbent article including the topsheet 2 and the absorbent core 4 configured in this way, when the absorbent core 4 absorbs the discharged excrement and swells, the first projections 241 exist in a depressed space defined by the central low-basis-weight portion 46, and the second projections 242 exist in a depressed space defined by the side low-basis-weight portion 47. The first projection 241 having a relatively large size exists in the depressed space with a relatively gentle slope. In contrast, the second projection 242 having a relatively small size exists in the depressed space with a relatively steep slope. Under such a state, the excrement can be smoothly induced into the space of the central low-basis-weight portion 46 along the gentle slope by the first projection 241. Even when the excrement leaks out of the space of the central low-basis-weight portion 46 in the width direction Y, the excrement is induced into the space of the side low-basis-weight portion 47 and is prevented from leaking. Even when the excrement is induced into the space of the side low-basis-weight portion 47, since the second projection 242 exists in the space with a relatively steep slope, the excrement induced into the space is effectively prevented from leaking out of the space by the second projection 242.

In a topsheet 2 shown in FIGS. 7(a) to 8(f), a central region 2C including first projections 241 is located at the central portion in the width direction Y, and extends in the longitudinal direction X. A pair of side regions 2S and 2S including second projections 242 are adjacent to the central region 2C, and extend in the longitudinal direction X.

Figure 7A:
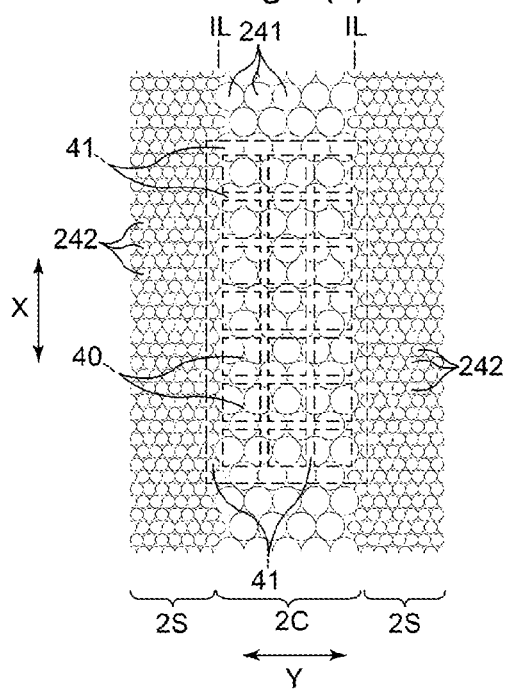
FIGS. 7(a) to 7(c) are plan views showing further another embodiment of a topsheet and an absorbent core used in the present invention.

An absorbent core 4 shown in FIG. 7(a) has a block structure having a groove-like space extending in the longitudinal direction X and the width direction Y on the skin-facing surface. In the absorbent core 4 of the block structure, the groove-like space is formed at a low-basis-weight portion 41, and the low-basis-weight portion 41 extends in the longitudinal direction X and the width direction Y and is formed in a grid shape in a plan view. Then, a plurality of small regions defined by the low-basis-weight portions 41 formed in the grid shape are high-basis-weight portions 40. In the embodiment shown in FIG. 7(a), a boundary IL between the central region 2C and the side region 2S of the topsheet 2 is disposed on the low-basis-weight portion 41 extending in the longitudinal direction X located at the outermost side in the width direction Y, and the topsheet 2 includes two types of projections, for example, the first projections 241 and the second projections 242 having different sizes in an overlapping region with the low-basis-weight portion 41.

Figure 7B:
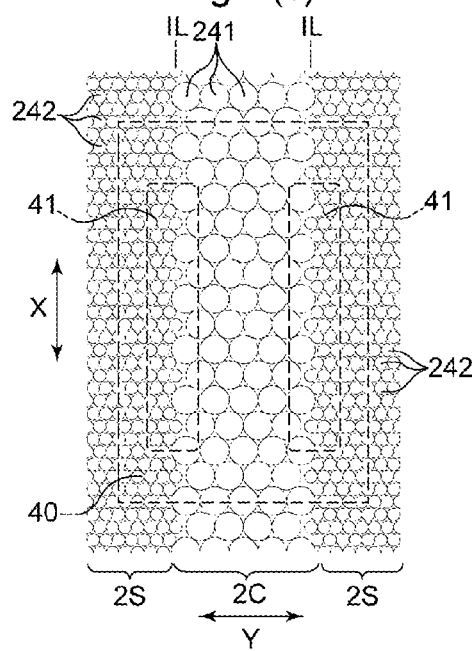

The absorbent core 4 shown in FIG. 7(b) includes a pair of low-basis-weight portions 41 and 41 located on laterally outer sides in the width direction Y and extend in the longitudinal direction X. The low-basis-weight portion 41 extends in the longitudinal direction X with a constant width. In the embodiment shown in FIG. 7(b), a boundary IL between the central region 2C and the side region 2S of the topsheet 2 is disposed on each of the low-basis-weight portions 41 extending in the longitudinal direction X, and the topsheet 2 includes two types of projections, for example, the first projections 241 and the second projections 242 having different sizes in an overlapping region with each of the low-basis-weight portions 41. The first projections 241 and the second projections 242 in the region have different lengths in the width direction Y. In detail, a length in the width direction Y of the second projection 242 located on the outer side in the width direction Y of each of the low-basis-weight portions 41 is shorter than a length in the width direction Y of the first projection 241 located on the central side in the width direction Y of each of the low-basis-weight portions 41.

Figure 7C:
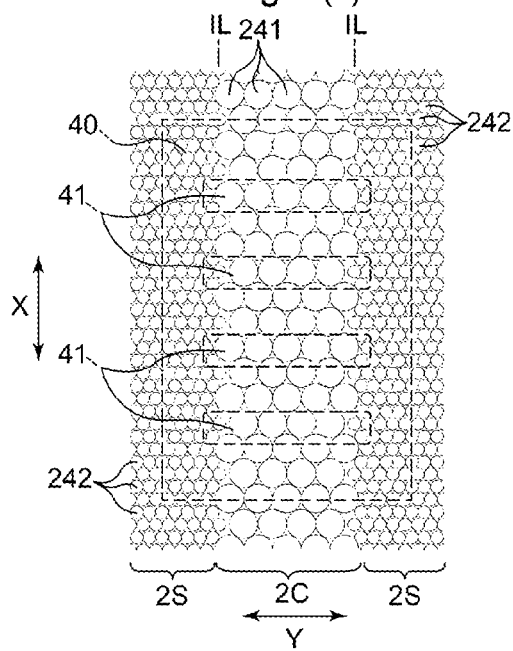

A plurality of low-basis-weight portions 41 included in the absorbent core 4 shown in FIG. 7(c) extend in the width direction Y with a constant width, and are disposed at intervals in the longitudinal direction X. In the embodiment shown in FIG. 7(c), a boundary IL between the central region 2C and the side region 2S of the topsheet 2 is disposed to intersect with the end portion in the width direction Y of each of the low-basis-weight portions 41 extending in the width direction Y, and the topsheet 2 includes two types of projections, for example, the first projections 241 and the second projections 242 having different sizes in an overlapping region with each of the low-basis-weight portions 41. The first projections 241 and the second projections 242 in the region have different lengths in the width direction Y. In detail, a length in the width direction Y of the second projection 242 located on the outer side in the width direction Y of each of the low-basis-weight portions 41 is shorter than a length in the width direction Y of the first projection 241 located on the central side in the width direction Y of each of the low-basis-weight portions 41.

The absorbent core 4 shown in FIG. 8(*d*) includes a pair of low-basis-weight portions 41 and 41 located on laterally outer sides in the width direction Y and extending in the longitudinal direction X. The pair of low-basis-weight portions 41 and 41 have lateral side edges facing each other and are projected in an arc shape toward the center in the width direction Y. In the embodiment shown in FIG. 8(*d*), a boundary IL between the central region 2C and the side region 2S of the topsheet 2 is disposed at an intersecting position with the arc-shaped lateral side edge in each of the low-basis-weight portions 41, and the topsheet 2 includes two types of projections, for example, the first projections 241 and the second projections 242 having different sizes in an overlapping region with each of the low-basis-weight portions 41. The first projections 241 and the second projections 242 in the region have different lengths in the width direction Y and also have different length in the longitudinal direction X. In detail, a length in the width direction Y of the second projection 242 located on the outer side in the width direction Y of each of the low-basis-weight portions 41 is shorter than a length in the width direction Y of the first projection 241 located on the central side in the width direction Y of each of the low-basis-weight portions 41. A length in the longitudinal direction X of the second projection 242 located on the outer side in the width direction Y of each of the low-basis-weight portions 41 is shorter than a length in the longitudinal direction X of the first projection 241 located on the central side in the width direction Y of each of the low-basis-weight portions 41.

The absorbent core 4 shown in FIG. 8(*e*) includes a pair of low-basis-weight portions 41 and 41 located on laterally outer sides in the width direction Y and extending in the longitudinal direction X. The pair of low-basis-weight portions 41 and 41 are projected in an arc shape toward the center in the width direction Y. In the embodiment shown in FIG. 8(*e*), a boundary IL between the central region 2C and the side region 2S of the topsheet 2 is disposed to intersect with the end portion in the longitudinal direction X of each of the low-basis-weight portions 41 extending in the longitudinal direction X, and the topsheet 2 includes two types of projections, for example, the first projections 241 and the second projections 242 having different sizes in an overlapping region with each of the low-basis-weight portions 41. The first projections 241 and the second projections 242 in the region have different lengths in the width direction Y and also have different length in the longitudinal direction X. In detail, a length in the width direction Y of the second projection 242 located on the outer side in the width direction Y of each of the low-basis-weight portions 41 is shorter than a length in the width direction Y of the first projection 241 located on the central side in the width direction Y of each of the low-basis-weight portions 41. A length in the longitudinal direction X of the second projection 242 located on the outer side in the width direction Y of each of the low-basis-weight portions 41 is shorter than a length in the longitudinal direction X of the first projection 241 located on the central side in the width direction Y of each of the low-basis-weight portions 41.

The absorbent core 4 shown in FIG. 8(*f*) includes a pair of low-basis-weight portions 41 and 41 extending toward one side in the width direction Y, from the center in the longitudinal direction X and the width direction Y, and the other pair of low-basis-weight portions 41 and 41 extending toward the other side in the width direction Y. The pair of low-basis-weight portions 41 and 41 are formed such that a distance therebetween gradually increases from the center toward the outer side in the width direction Y. In the embodiment shown in FIG. 8(*f*), a boundary IL between the central region 2C and the side region 2S of the topsheet 2 is disposed to intersect with the each of the pair of low-basis-weight portions 41 and 41, and the topsheet 2 includes two types of projections, for example, the first projections 241 and the second projections 242 having different sizes in an overlapping region with each of the low-basis-weight portions 41. The first projections 241 and the second projections 242 in the region have different lengths in the width direction Y and also have different length in the longitudinal direction X. In detail, a length in the width direction Y of the second projection 242 located on the outer side in the width direction Y of each of the low-basis-weight portions 41 is shorter than a length in the width direction Y of the first projection 241 located on the central side in the width direction Y of each of the low-basis-weight portions 41. A length in the longitudinal direction X of the second projection 242 located on the outer side in the width direction Y of each of the low-basis-weight portions 41 is shorter than a length in the longitudinal direction X of the first projection 241 located on the central side in the width direction Y of each of the low-basis-weight portions 41.

In the topsheet 2 shown in FIG. 8(*g*), a central region 2A including a plurality of first projections 241 is located at a central portion in the longitudinal direction X and extends in the width direction Y. A pair of end regions 2T and 2T including a plurality of second projections 242 are adjacent to the central region 2A and extend in the width direction Y. The absorbent core 4 shown in FIG. 8(*g*) includes a pair of low-basis-weight portions 41 and 41 located at laterally outer sides in the width direction Y and extending in the longitudinal direction X. The low-basis-weight portions 41 is formed to continuously extend in the longitudinal direction X. In the embodiment shown in FIG. 8(*g*), a boundary IL between the central region 2A and the end region 2T of the topsheet 2 is disposed to intersect with the end portion in the longitudinal direction X of each of the low-basis-weight portions 41 extending in the longitudinal direction X, and the topsheet 2 includes two types of projections, for example, the first projections 241 and the second projections 242 having different sizes in an overlapping region with each of the low-basis-weight portions 41. The first projections 241 and the second projections 242 in the region have different lengths in the longitudinal direction X. Regarding lengths in the longitudinal direction X of the first projection 241 and the second projection 242, the length of the second projection 242 located on the outer side in the longitudinal direction X is shorter than the length of the first projection 241 located on the central side in the longitudinal direction X.

The above-described effects can also be obtained by the embodiments shown in FIGS. 7(*a*) to 8(*g*).

The topsheet 2 having the projecting-and-depressed structure as described above can be manufactured using an apparatus shown in FIG. 2 of Japanese Patent Laid-Open No. 2005-111908, for example. In such an apparatus, a first roller and a second roller, peripheral surfaces of which are meshed with each other, are disposed in a meshed state. Further, the apparatus includes an anvil roll disposed to abut on the peripheral surface of the first roller. Using the apparatus, a continuous upper nonwoven fabric 21 is supplied between the first roller and the second roller, and the upper nonwoven fabric 21 is deformed into an uneven shape. Thereafter, the upper nonwoven fabric 21 is moved from the meshed portion along the peripheral surface of the first roller, and then a continuous lower nonwoven fabric 22 is supplied to overlap the uneven-shaped upper nonwoven fabric 21, thereby both sheets are nipped between a projection of the first roller and a heat roller under heating. The upper nonwoven fabric 21 and the lower nonwoven fabric 22 are partially joined by the nipping, thereby the topsheet 2 is obtained. When a projection 24 includes a first projection 241 and a second projection 242, during deformation into the uneven shape, for example, the central portion and the sides in the width direction of the upper nonwoven fabric 21 can be formed by making the uneven shape of the first roller and the second roller and the pattern of the joined portion formed by the first roller and the heat roller different.

Examples of the upper nonwoven fabric 21 and the lower nonwoven fabric 22 forming the topsheet 2 may include an air-through nonwoven fabric, a spunbond nonwoven fabric, a spunlace nonwoven fabric, a melt-blown nonwoven fabric, a resin-bonded nonwoven fabric, and a needle punch nonwoven fabric. Such examples may include a laminated body in which two or more kinds of these nonwoven fabrics are combined, or a laminated body in which these nonwoven fabrics and a film are combined. The air-through nonwoven fabric or the spunbond nonwoven fabric are preferably used. A basis weight of each of the upper nonwoven fabric 21 and the lower nonwoven fabric 22 is preferably 10 $g/m^2$ or more and more preferably 15 $g/m^2$ or more, and is preferably 40 $g/m^2$ or less and more preferably 35 $g/m^2$ or less. The types of the nonwoven fabrics forming the upper nonwoven fabric 21 and the lower nonwoven fabric 22 may be the same or different.

Further, as a method of producing the absorbent core 4 including the low-basis-weight portions 41 as described above, for example, a method disclosed in Japanese Patent Laid-Open No. 2013-059373 can be adopted.

The absorbent article of the present invention is not limited to the above-described embodiments shown in FIGS. 1 and 2, FIG. 4, and FIGS. 6 to 8, and can be appropriately modified. In addition, the component requirements in the above-described embodiments shown in FIGS. 1 and 2, FIG. 4, and FIGS. 6 to 8 can be appropriately combined and implemented in the range of the gist of the present invention.

In the embodiments described above, the absorbent core 4 includes the plurality of low-basis-weight portions 41 extending in one direction, but may include only one low-basis-weight portion 41 extending in one direction, for example.

In the embodiments described above, the topsheet 2 is a sheet having the projecting-and-depressed structure formed using two nonwoven fabrics of the upper nonwoven fabric 21 including a large number of projections 24 and the substantially flat lower nonwoven fabric 22, but may be a sheet having a projecting-and-depressed structure formed using one nonwoven fabric. In addition, the shapes of projection-depression are not also limited to those shown in the embodiments described above.

The absorbent article according to the above-described embodiments of the present invention will be further disclosed below.

<1>

An absorbent article comprising: an absorbent core; and a topsheet disposed on a skin-facing surface of the absorbent core and having a projecting-and-depressed structure on the skin-facing surface, wherein the absorbent core includes one or a plurality of low-basis-weight portions extending in one direction and having a relatively lower basis weight than other parts of the absorbent core, and in a plan view, the topsheet includes a plurality of types of projections having different sizes in an overlapping region with the low-basis-weight portions.

<2>

The absorbent article as set forth in clause <1>, wherein the absorbent article has a longitudinal direction corresponding to a front-rear direction of a wearer and a width direction orthogonal to the longitudinal direction, and a projection having a relatively large size is located on a center in the width direction, and a projection having a relatively small size is located on both outer sides in the width direction.

<3>

The absorbent article as set forth in clause <1>, wherein the absorbent article has a longitudinal direction corresponding to a front-rear direction of a wearer and a width direction orthogonal to the longitudinal direction, and a projection having a relatively large size is located on a center in the longitudinal direction, and a projection having a relatively small size is located on both outer sides in the longitudinal direction.

<4>

The absorbent article as set forth in clause <1>, wherein the absorbent article has a longitudinal direction corresponding to a front-rear direction of a wearer and a width direction orthogonal to the longitudinal direction, and a length in the width direction of a projection located on outer sides in the width direction is shorter than a length in the width direction of a projection located on a center in the width direction.

<5>

The absorbent article as set forth in clause <4>, wherein the low-basis-weight portion extends in the longitudinal direction.

<6>

The absorbent article as set forth in clause <5>, wherein the low-basis-weight portions include a first low-basis-weight portion located on a center in the width direction of the absorbent core and a pair of second low-basis-weight portions located on laterally outer sides in the width direction from the first low-basis-weight portion, and a length in the width direction of the projection located in each of the second low-basis-weight portions is shorter than a length in the width direction of the projection located in the first low-basis-weight portion.

<7>

The absorbent article as set forth in clause <5>, wherein the absorbent core includes a pair of low-basis-weight portions located on laterally outer sides in the width direction, and a length in the width direction of the projection located on outer sides in the width direction of each of the low-basis-weight portions is shorter than a length in the width direction of the projection located on a center in the width direction of each of the low-basis-weight portions.

<8>
The absorbent article as set forth in clause <5>, wherein the absorbent core includes a pair of low-basis-weight portions that are projected in an arc shape, and
a length in the width direction of the projection located on outer sides in the width direction of each of the low-basis-weight portions is shorter than a length in the width direction of the projection located on a center in the width direction of each of the low-basis-weight portions.

<9>
The absorbent article as set forth in clause <7> or <8>, wherein the topsheet includes a first projection and a second projection, a length in the width direction of the first projection is shorter than a length in the width direction of the second projection, the second projection is disposed in a central region in the width direction, and the first projection is disposed in side regions located on both outer sides in the width direction of the central region.

<10>
The absorbent article as set forth in clause <4>, wherein the low-basis-weight portion extends in the width direction.

<11>
The absorbent article as set forth in clause <10>, wherein a length in the width direction of a projection located on side regions in the width direction of the low-basis-weight portion is shorter than a length in the width direction of a projection located in a central region in the width direction of the low-basis-weight portion.

<12>
The absorbent article as set forth in clause <11>, wherein the topsheet includes a first projection and a second projection, a length in the width direction of the first projection is shorter than a length in the width direction of the second projection, the first projection is disposed in side regions in the width direction, and the second projection is disposed in a central region in the width direction.

<13>
The absorbent article as set forth in clause <1>, wherein the absorbent article has a longitudinal direction corresponding to a front-rear direction of a wearer and a width direction orthogonal to the longitudinal direction,
the low-basis-weight portion extends in the longitudinal direction,
the topsheet includes a plurality of types of projections having different sizes in an overlapping region with the low-basis-weight portion, and
a length in the longitudinal direction of a projection located on outer sides in the longitudinal direction is shorter than a length in the longitudinal direction of a projection located on a center in the longitudinal direction.

<14>
The absorbent article as set forth in clause <13>, wherein the low-basis-weight portion extends in the longitudinal direction.

<15>
The absorbent article as set forth in clause <14>, wherein a length in the longitudinal direction of the projection located in an end region in the longitudinal direction of the low-basis-weight portion is shorter than a length in the longitudinal direction of the projection located in a central region in the longitudinal direction of the low-basis-weight portion.

<16>
The absorbent article as set forth in clause <14>, wherein the topsheet includes a first projection and a second projection, a length in the longitudinal direction of the first projection is shorter than a length in the longitudinal direction of the second projection, the first projection is disposed in an end region in the longitudinal direction, and the second projection is disposed in a central region in the longitudinal direction.

<17>
The absorbent article as set forth in clause <13>, wherein the low-basis-weight portion extends in the width direction.

<18>
The absorbent article as set forth in clause <17>, wherein the low-basis-weight portions include a first low-basis-weight portion located on the center in the longitudinal direction of the absorbent core and a pair of second low-basis-weight portions located on front-rear outer sides in the longitudinal direction from the first low-basis-weight portion, and
a length in the longitudinal direction of the projection located on the outer sides in the longitudinal direction of each of the second low-basis-weight portions is shorter than a length in the longitudinal direction of the projection located on the center in the longitudinal direction of the second low-basis-weight portions.

<19>
The absorbent article as set forth in clause <18>, wherein the topsheet includes a first projection and a second projection, a length in the longitudinal direction of the first projection is shorter than a length in the longitudinal direction of the second projection, the first projection is disposed in the second low-basis-weight portions, and the second projection is disposed in the first low-basis-weight portion.

<20>
The absorbent article as set forth in any one of clauses <1>, <2>, <3>, <4>, <5>, <10>, and <13>, wherein the absorbent article has a longitudinal direction corresponding to a front-rear direction of a wearer and a width direction orthogonal to the longitudinal direction,
the topsheet is provided with a central region that is a center in the width direction and extends in the longitudinal direction and a pair of side regions that are adjacent to the central region and extend in the longitudinal direction,
a length in the width direction of the projection provided in the central region is longer than a length in the width direction of the projection provided in the side regions,
the absorbent core includes the pair of low-basis-weight portion extending in the longitudinal direction at intervals in the width direction,
the pair of low-basis-weight portions are longer at an end portion in the longitudinal direction than at a central portion in the longitudinal direction, and
when a distance between the pair of low-basis-weight portions at the central portion in the longitudinal direction is defined as A, a distance between the pair of low-basis-weight portions at the end portion in the longitudinal direction is defined as C, and a width of the central region is defined as B, a relation of A<B<C is established.

<21>
The absorbent article as set forth in clause <1>, wherein the absorbent core includes a plurality of low-basis-weight portions that do not intersect with each other, and the low-basis-weight portions include a first low-basis-weight portion and a second low-basis-weight portion, and
a length in the width direction of the projection located in the first low-basis-weight portion is different from a length in the width direction of the projection located in the second low-basis-weight portion.

<22>

The absorbent article as set forth in any one of clauses <1> to <21>, wherein the topsheet has a layered structure in which an upper nonwoven fabric located on a skin side of a wearer and a lower nonwoven fabric located on a side far from the skin of the wearer are joined in a worn state, the projection protrudes such that the upper nonwoven fabric is separated from the lower nonwoven fabric at a region other than a joined portion where the upper nonwoven fabric and the lower nonwoven fabric are joined, and a total area of the joined portion surrounding the projection having a relatively large size is larger than a total area of the joined portion surrounding the projection having a relatively small size.

INDUSTRIAL APPLICABILITY

According to the absorbent article of the present invention, excrement is easily induced into the low-basis-weight portions formed in the absorbent core, and the excrement induced into the low-basis-weight portions is prevented from leaking out of the low-basis-weight portion, so that the leakage of the excrement can be prevented more reliably.

The invention claimed is:

1. An absorbent article comprising:
   an absorbent core; and
   a topsheet disposed on a skin-facing surface of the absorbent core and having a projecting-and-depressed structure on the skin-facing surface, wherein
   the absorbent article has a longitudinal direction corresponding to a front-rear direction of a wearer and a width direction orthogonal to the longitudinal direction,
   the absorbent core includes a pair of low-basis-weight portions extending in the longitudinal direction at intervals in the width direction and having a relatively lower basis weight than other parts of the absorbent core,
   in a plan view, the topsheet includes a plurality of projections having different sizes in an overlapping region with the low-basis-weight portions of the absorbent core,
   the topsheet is provided with a central region that is a center in the width direction and extends in the longitudinal direction and a pair of side regions that are adjacent to the central region and extend in the longitudinal direction,
   a length in the width direction of one of the plurality of topsheet projections provided in the central region is longer than a length in the width direction of one of the plurality of topsheet projections provided in the side regions, and
   when a width distance between center-facing inward side edges of the pair of low-basis-weight portions at the central portion in the longitudinal direction is defined as A, a width distance between center-facing inward side edges of the pair of low-basis-weight portions at the end portion in the longitudinal direction is defined as C, and a width of the central region of the topsheet is defined as B, a relation of A<B<C is established.

2. The absorbent article according to claim 1, wherein
   the absorbent core further includes a low-basis-weight portion located on a center in the width direction of the absorbent core that is between the pair of low-basis-weight portions that are located on laterally outer sides in the width direction of the absorbent core, and
   a length in the width direction of the topsheet projections located in each of the pair of low-basis-weight portions located on laterally outer sides in the width direction of the absorbent core is shorter than a length in the width direction of the topsheet projections located in the low-basis-weight portion located on a center in the width direction of the absorbent core.

3. The absorbent article according to claim 1, wherein
   the pair of low-basis-weight portions, which each have an arc shape, and
   a length in the width direction of one or more of the plurality of topsheet projections located at the overlapping region of each of the arc shape low-basis-weight portions is shorter than a length in the width direction of one or more of the plurality of topsheet projections located at the overlapping region on a center in the width direction of each of the low-basis-weight portions.

4. The absorbent article according to claim 1, wherein
   the topsheet includes a first projection and a second projection, a length in the width direction of the first projection is shorter than a length in the width direction of the second projection, the second projection is disposed in the central region in the width direction, and the first projection is disposed in the side regions located on both outer sides in the width direction of the central region.

5. The absorbent article according to claim 1, wherein
   the topsheet includes a plurality of projections having different sizes in an overlapping region with the pair of low-basis-weight portions, and
   a length in the longitudinal direction of a topsheet projection located on outer sides in the longitudinal direction is shorter than a length in the longitudinal direction of a topsheet projection located on a center of the topsheet in the longitudinal direction.

6. The absorbent article according to claim 5, wherein
   a length in the longitudinal direction of a topsheet projection located in an end region in the longitudinal direction of the pair of low-basis-weight portions is shorter than a length in the longitudinal direction of a topsheet projection located in the central region of the topsheet in the longitudinal direction of the pair of low-basis-weight portions.

7. The absorbent article according to claim 5, wherein
   the topsheet includes a first projection and a second projection, a length in the longitudinal direction of the first projection is shorter than a length in the longitudinal direction of the second projection, the first projection is disposed in an end region in the longitudinal direction, and the second projection is disposed in a central region in the longitudinal direction.

8. The absorbent article according to claim 1, wherein
   the topsheet has a layered structure in which an upper nonwoven fabric located on a skin side of a wearer and a lower nonwoven fabric located on a side far from the skin of the wearer are joined in a worn state,
   the projection protrudes such that the upper nonwoven fabric is separated from the lower nonwoven fabric at a region other than a joined portion where the upper nonwoven fabric and the lower nonwoven fabric are joined, and
   a total area of the joined portion surrounding the projection having a relatively large size is larger than a total area of the joined portion surrounding the projection having a relatively small size.

* * * * *